(12) United States Patent
Urbanowicz et al.

(10) Patent No.: US 9,091,667 B2
(45) Date of Patent: Jul. 28, 2015

(54) DETECTION OF PARTICLE CONTAMINATION ON WAFERS

(71) Applicant: GLOBALFOUNDRIES Inc., Grand Cayman (KY)

(72) Inventors: Adam Michal Urbanowicz, Dresden (DE); Carsten Hartig, Meerane (DE); Daniel Fischer, Dresden (DE)

(73) Assignee: GLOBALFOUNDRIES Inc., Grand Cayman (KY)

( * ) Notice: Subject to any disclaimer, the term of this patent is extended or adjusted under 35 U.S.C. 154(b) by 0 days.

(21) Appl. No.: 14/063,531

(22) Filed: Oct. 25, 2013

(65) Prior Publication Data

US 2015/0115153 A1    Apr. 30, 2015

(51) Int. Cl.
*G01N 21/00* (2006.01)
*G01N 21/95* (2006.01)
*G01N 23/00* (2006.01)

(52) U.S. Cl.
CPC ............ *G01N 21/9501* (2013.01); *G01N 23/00* (2013.01)

(58) Field of Classification Search
CPC .......... G01N 21/9501; G01N 21/8806; G01N 21/94; G01N 21/956; G01N 21/88
USPC ...................................... 356/237.1
See application file for complete search history.

(56) References Cited

U.S. PATENT DOCUMENTS

| | | | |
|---|---|---|---|
| 6,742,168 B1* | 5/2004 | Nariman | 438/7 |
| 2003/0223072 A1* | 12/2003 | Schulz | 356/446 |
| 2008/0024766 A1* | 1/2008 | Mieher et al. | 356/73 |
| 2009/0187383 A1* | 7/2009 | Li et al. | 702/191 |

OTHER PUBLICATIONS

Vaid et al., "A Holistic Metrology Approach: Hybrid Metrology Utilizing Scatterometry, CD-AFM and CD-SEM," Proc. of SPIE, vol. 7971, 797103-1, 2011.
Vaid et al., "Improved Scatterometry Time to Solution for Leading-Edge Logic Applications," ASMC 2010, pp. 341-346, 2010.

* cited by examiner

*Primary Examiner* — Tarifur Chowdhury
*Assistant Examiner* — Md Rahman
(74) *Attorney, Agent, or Firm* — Amerson Law Firm, PLLC

(57) ABSTRACT

A method of the detection of particle contamination on a semiconductor wafer is provides which includes examining an area of the semiconductor wafer by a metrology system comprising a scatterometry or ellipsometry/reflectometry tool to obtain measured metrology data, comparing the measured metrology data with reference metrology data and determining the presence of particle contamination in the examined area of the semiconductor wafer based on the comparison of the measured metrology data with the reference metrology data.

15 Claims, 8 Drawing Sheets

DETECTION OF PARTICLE CONTAMINATION ON WAFERS

BACKGROUND OF THE INVENTION

1. Field of the Invention

Generally, the present disclosure relates to the field of the manufacture of integrated circuits and semiconductor devices, and, more particularly, to the detection of particle contamination of semiconductor wafers.

2. Description of the Related Art

The fabrication of advanced integrated circuits, such as CPUs, storage devices, ASICs (application specific integrated circuits) and the like, requires the formation of a large number of circuit elements on a given chip area according to a specified circuit layout. In a wide variety of electronic circuits, field effect transistors represent one important type of circuit element that substantially determines performance of the integrated circuits. Generally, a plurality of process technologies are currently practiced for forming field effect transistors, wherein, for many types of complex circuitry, MOS technology is currently one of the most promising approaches due to the superior characteristics in view of operating speed and/or power consumption and/or cost efficiency. During the fabrication of complex integrated circuits using, for instance, MOS technology, millions of transistors, e.g., N-channel transistors and/or P-channel transistors, are formed on a substrate including a crystalline semiconductor layer.

The manufacturing of semiconductor devices requires high levels of cleanliness during the numerous manufacturing processes. For example, the surface of semiconductor wafers must be thoroughly cleaned of particle contaminants prior to processing. Further, films, such as dielectric films or metal films deposited on the semiconductor wafer, must also be thoroughly cleaned of particle contaminants. If not removed, contaminants on wafers and films may affect device performance characteristics and cause device failures to occur at faster rates than expected otherwise. Therefore, many of the processing steps are conducted in "clean rooms" to reduce possible particle contamination.

Nevertheless, semiconductor devices can become contaminated, and rendered defective, by contaminants during the various process steps. For example, during the various processing steps, contaminants may be introduced from the numerous processing tools because of incomplete cleansing of reagents from the tools.

Industry requirements for some processes, such as EUV lithography, require zero defects above 50 nm in size, since these are considered killer defects, and only a few defects can be tolerated between 20 nm and 50 nm. The defect requirements for other applications are less stringent, though the trends are driving towards less than 10 particles at continuously smaller sizes. The reduction of particles at such small sizes is producing extreme challenges for original equipment manufacturers (OEMs) as they must tightly control the performance of every component within the equipment, in addition to reducing process defects. The component suppliers face additional challenges as they not only have to meet the stringent performance specifications but also must improve performance based on continuously changing process latitudes and chemistries of end users.

One of the biggest challenges with such small defects is inspection and metrology. In the art, it is known to employ dark-field and bright-field microscopes or electron beam microscopes, possibly combined with a critical-dimension scanning or transmission microscope. However, sensibility for the detection of contaminating particles is not satisfying and state-of-the-art inspection tools can find defects only down to 30 nm on wafers and masks. Inspection tools capable of detecting smaller sizes are presently not available. Inspection and failure analysis tools that are capable of detecting defect sources below 50 nm are enormously costly, which causes a large infrastructure gap for suppliers working in component and material development. Lacking that infrastructure, it is very difficult for many OEMs and subsystem, component and material suppliers to reduce defect sources and improve defect performance.

Reducing particle contamination from semiconductor processing tools quickly is, therefore, of high importance. Tool downtime can be very costly as semiconductor processing is slowed or halted while the contamination source is located and cleaned. Further, accurately determining the source and eliminating the particle contamination is vital for producing high-quality semiconductor devices. Therefore, quickly and accurately determining the source of particle contamination in a semiconductor processing tool and returning the tool to service is of great importance.

In view of the situation described above, the present disclosure provides techniques for determining particle contamination of a semiconductor wafer in a reliable and fast, as well as non-destroying, manner, in particular, with high sensitivity and down to very small scales of below 30 nm.

SUMMARY OF THE INVENTION

The following presents a simplified summary of the invention in order to provide a basic understanding of some aspects of the invention. This summary is not an exhaustive overview of the invention. It is not intended to identify key or critical elements of the invention or to delineate the scope of the invention. Its sole purpose is to present some concepts in a simplified form as a prelude to the more detailed description that is discussed later.

Metrology techniques are conventionally used for overlay control and determination of the spatial dimensions of features, for example, the thicknesses of polysilicon or nitride layers, a critical dimension of a polysilicon layer or a width of a sidewall spacer formed at a sidewall of a gate electrode. The inventors of the present invention surprisingly found out that metrology techniques may be useful for particle determination. An atypical use of present scatterometry or ellipsometry tools allows for an unprecedented sensitivity and reliability of contamination particle detection on processed semiconductor wafers. An illustrative method of the detection of particle contamination on a semiconductor wafer includes examining an area of the semiconductor wafer by a metrology system comprising a scatterometry or ellipsometry/reflectometry tool to obtain measured metrology data, comparing the measured metrology data with reference metrology data and determining the presence of particle contamination in the examined area of the semiconductor wafer based on the comparison of the measured metrology data with the reference metrology data.

The semiconductor wafer is a wafer processed for the manufacture of semiconductor devices and may comprise a periodic structure, for example, a grating structure, for example, in the form of a group of transistor gate electrodes. The determination of particle contamination may be based on the comparison of reference reflection profiles and reflection profiles generated based on the measurement of light reflected from the semiconductor wafer or based on the comparison of reference profiles of polarization or change of polarization and measured profiles of polarization or change of polarization. The reference profiles of polarization or change of polarization or reference reflection profiles may be provided based on models, for example, comprising structure models known in the art.

Furthermore, a metrology tool adapted to receive a semiconductor wafer is provided, including a light source adapted to illuminate at least a portion of the semiconductor wafer, a detector adapted to measure light reflected from the semiconductor wafer, a database storing reference metrology data and a data processing unit adapted to obtain measured metrology data based on the reflected light measured by the detector, compare the measured metrology data with the reference metrology data and determine the presence of particle contamination in the examined area of the semiconductor wafer based on the comparison of the measured metrology data with reference metrology data. The light source and the detector may be in a scatterometry or ellipsometry/reflectometry tool.

BRIEF DESCRIPTION OF THE DRAWINGS

The disclosure may be understood by reference to the following description taken in conjunction with the accompanying drawings, in which like reference numerals identify like elements, and in which.

Figure 1:
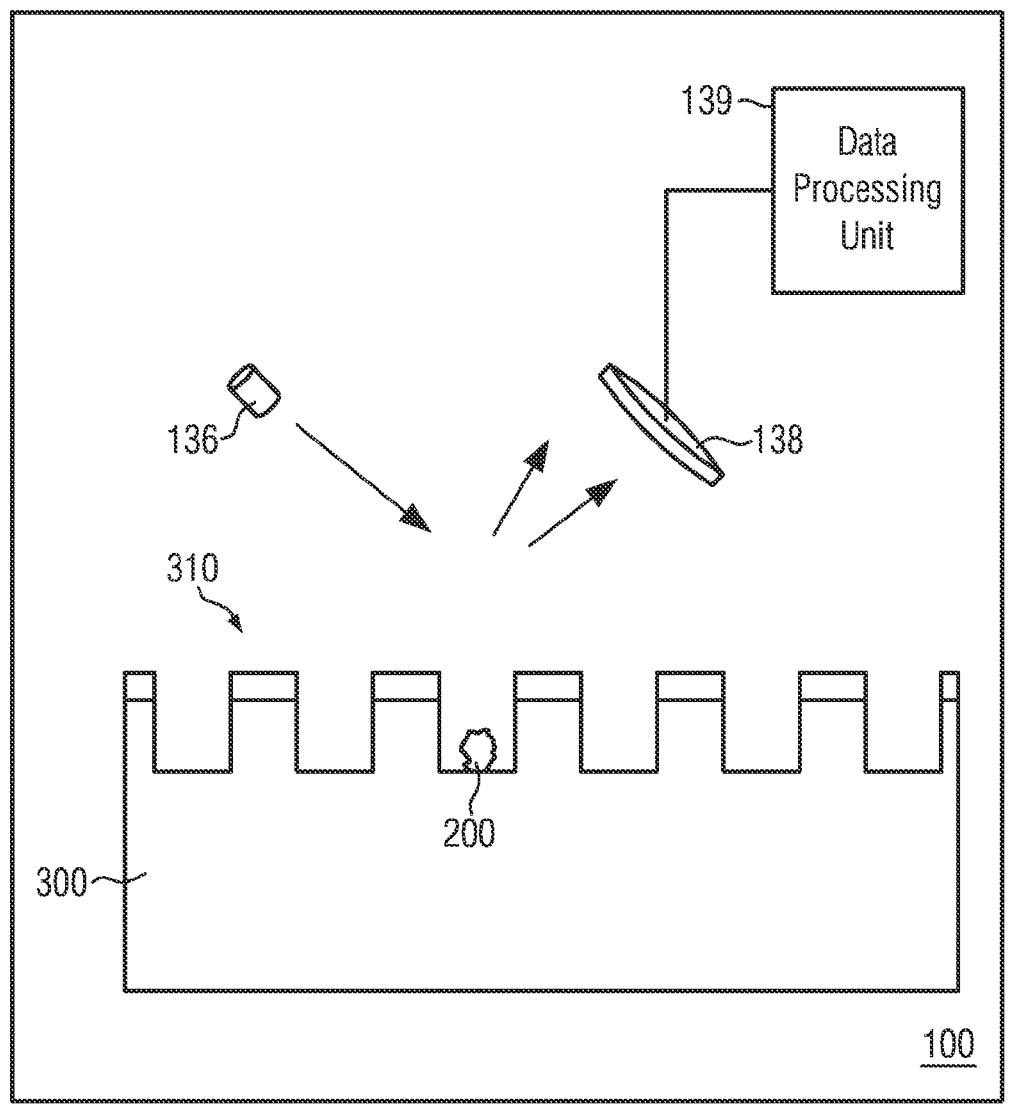
FIG. 1 illustrates a metrology tool comprising a scatterometry tool according to an example of the present invention.

While the subject matter disclosed herein is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION

Various illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The present disclosure will now be described with reference to the attached figures. Various structures, systems and devices are schematically depicted in the drawings for purposes of explanation only and so as to not obscure the present disclosure with details which are well known to those skilled in the art. Nevertheless, the attached drawings are included to describe and explain illustrative examples of the present disclosure. The words and phrases used herein should be understood and interpreted to have a meaning consistent with the understanding of those words and phrases by those skilled in the relevant art. No special definition of a term or phrase, i.e., a definition that is different from the ordinary or customary meaning as understood by those skilled in the art, is intended to be implied by consistent usage of the term or phrase herein. To the extent that a term or phrase is intended to have a special meaning, i.e., a meaning other than that understood by skilled artisans, such a special definition shall be expressively set forth in the specification in a definitional manner that directly and unequivocally provides the special definition for the term or phrase.

As will be readily apparent to those skilled in the art upon a complete reading of the present application, the present methods are applicable to a variety of technologies, e.g., NMOS, PMOS, CMOS, etc.

The present disclosure provides an atypical use of scatterometry or Ellipsometry/reflectometry tools for the detection of particle contamination, for example, the detection of individual particles on a periodic structure, for example, a grating structure, formed on a semiconductor wafer.

It is noted that in ellipsometry, light polarization measurement versus light wavelength is employed, whereas in reflectometry, light intensity measurement versus light wavelength is employed. Both ellipsometry and reflectometry are envisaged as equivalent tools in this application. Scatterometry, in principle, can make use of both ellipsometry and reflectometry. Moreover, a metrology tool used for the detection of particle contamination can make use of both ellipsometry and reflectometry measurements. Generally, the wavelengths of light used by the metrology tool (scatterometry or ellipsometry/reflectometry tool) can lie in the following ranges, for example: x-ray, vacuum UV, UV, visible, IR Far IR.

FIG. 1 illustrates a metrology tool comprising a scatterometry tool 100 configured to receive a semiconductor wafer 300 having a grating structure 310 formed thereon according to an example of the present invention. The grating structure 310 may be features formed in a production device on the semiconductor wafer 300 (e.g., gate electrodes, shallow trench isolation structures, interconnection trenches), or alternatively, the grating structure 310 may be a test structure having dimensions and construction materials similar to a production device. For example, the grating structure 310 may basically consist of gate lines running perpendicularly on top of fin lines of FinFETs. Fin lines may be formed of an oxide layer on top of SOI (silicon-on-insulator), whereas polysilicon lines may contain a gate oxide, metal gate and/or SiN cap. Polysilicon critical dimensions and Fin critical dimensions are critical measurement parameters in conventional scatterometry examination.

Furthermore, the scatterometry tool 100 comprises a light source 136 and a detector 138. The detector 138 is connected for data transfer with a data processing unit 139. Optical measurements such as the intensity or phase of the light reflected from the grating structure 310 can be transmitted from the detector 138 to the data processing unit 139. The scatterometry tool 100 may additionally comprise one or more lenses (not shown) for conditioning the light radiated on the grating structure 310 and reflected from the same.

The scatterometry tool 100 may use monochromatic light, white light or some other wavelength or combinations of wavelengths, depending on the specific implementation. The angle of incidence of the light may also vary, depending on the specific implementation. The light analyzed by the scatterometry tool 100 typically includes a reflected component (i.e., incident angle equals reflected angle) and a refracted component (i.e., incident angle does not equal the reflected angle). For purposes of discussion here, the term "reflected" light is meant to encompass both components.

Variations in the characteristics of the grating structure 310 cause changes in the reflection profile (e.g., intensity vs. wavelength-tan ($\delta$), phase vs. wavelength-sin ([$\psi$]), where $\delta$ and $\psi$ are common scatterometry outputs known to those of ordinary skill in the art) measured by the scatterometry tool 100. The particular reflection profile expected for any structure depends on the specific geometry of the grating structure 310 and the parameters of the measurement technique employed by the scatterometry tool 100 (e.g., light bandwidth, angle of incidence, etc.). Reference reflection profiles are typically calculated theoretically by employing Maxwell's equations based on the topology and geometry of the grating structure 310. The process for generating reference reflection profiles is well known to those of ordinary skill in the art. The reference reflection profiles may also be generated empirically by measuring reflection profiles of sample wafers and subsequently characterizing the measured wafers by some other destructive or non-destructive examination technique.

The data processing unit 139 may include one or more processors coupled to one or more memories. The data processing unit 139 may include, for example, multiple discrete, networked computer systems. The data processing unit 139 may comprise structure model software, modeling software and a user interface. The structure model software, modeling software and user interface are typically software comprising instructions suitable for execution by the one or more processors of the data processing unit 139. The structure model software is software that interfaces with the user interface to allow a user to define a structure model. The user interface interfaces with one or more displays in order to provide access to the structure model software and to the modeling software and to display the output structure parameters. The structure model software provides the structure model to the modeling software. The modeling software analyzes the structure model in order to determine expected metrology data (e.g., expected reflectivity data, expected ellipsometry data, or both). The modeling software also analyzes the detector output signals to determine measured metrology data (e.g., measured reflectivity data, measured ellipsometry data, or both). In the art, characteristics of the semiconductor wafer, such as thicknesses of formed layers and overlay characteristics, are determined from a comparison of a measured reflection profile and stored reference reflection profiles by matching the measured reflection profile to the closest reference reflection profile.

However, according to one example of the present invention, the scatterometry tool 100 is used for the detection of particle contamination 200. It turned out that if, in a particular area of the semiconductor wafer 300 or the grating structure 310, respectively, some contaminating particle 200 is present, significant misfit of the reflection profiles generated for that area with the stored reference reflection profiles results. This misfit that might be quantified in terms of a significantly low goodness of fitting can be used as an indicator for the presence of a contaminating particle 200.

Figure 2:
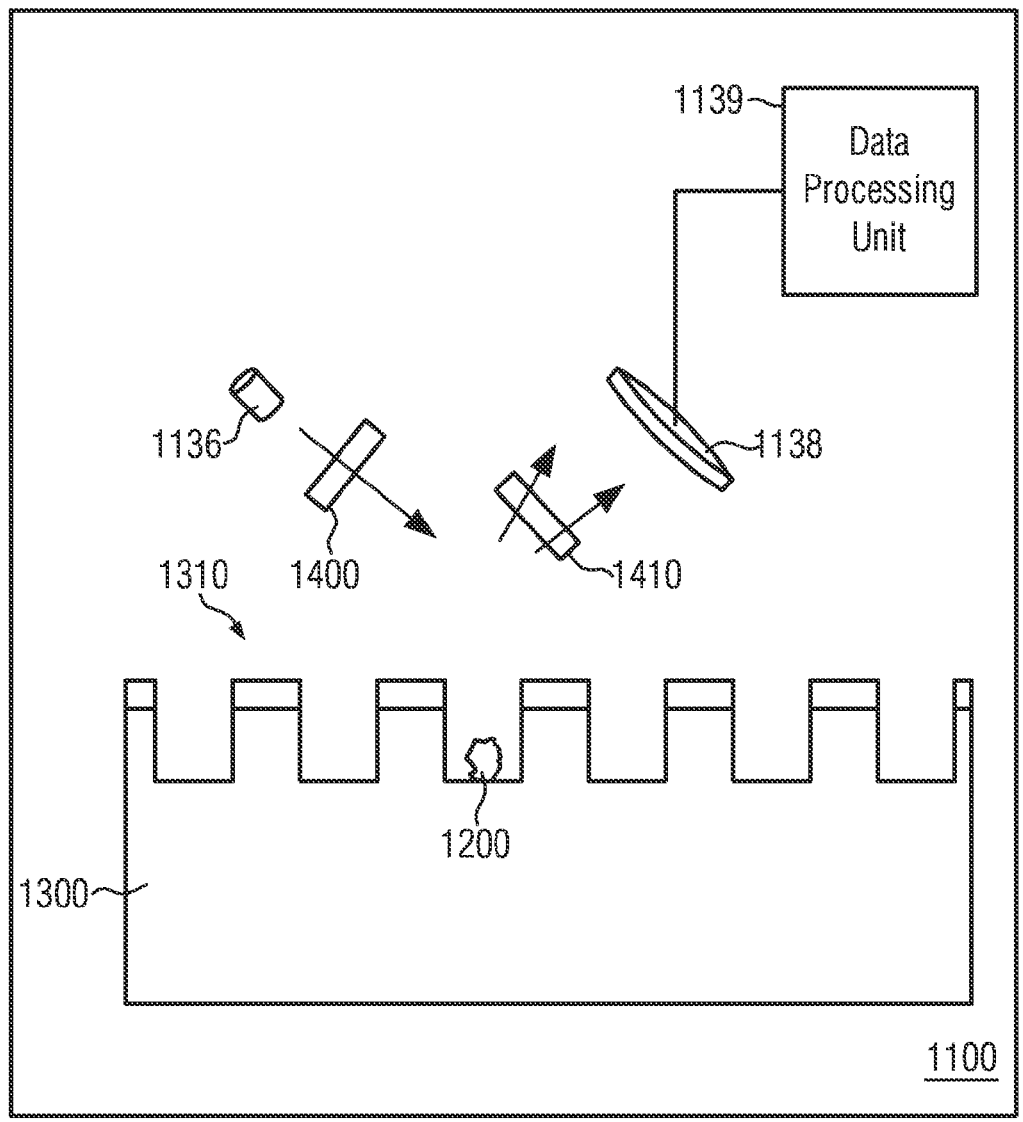
FIG. 2 illustrates a metrology tool comprising an ellipsometry tool according to an example of the present invention.
Figure 3A:
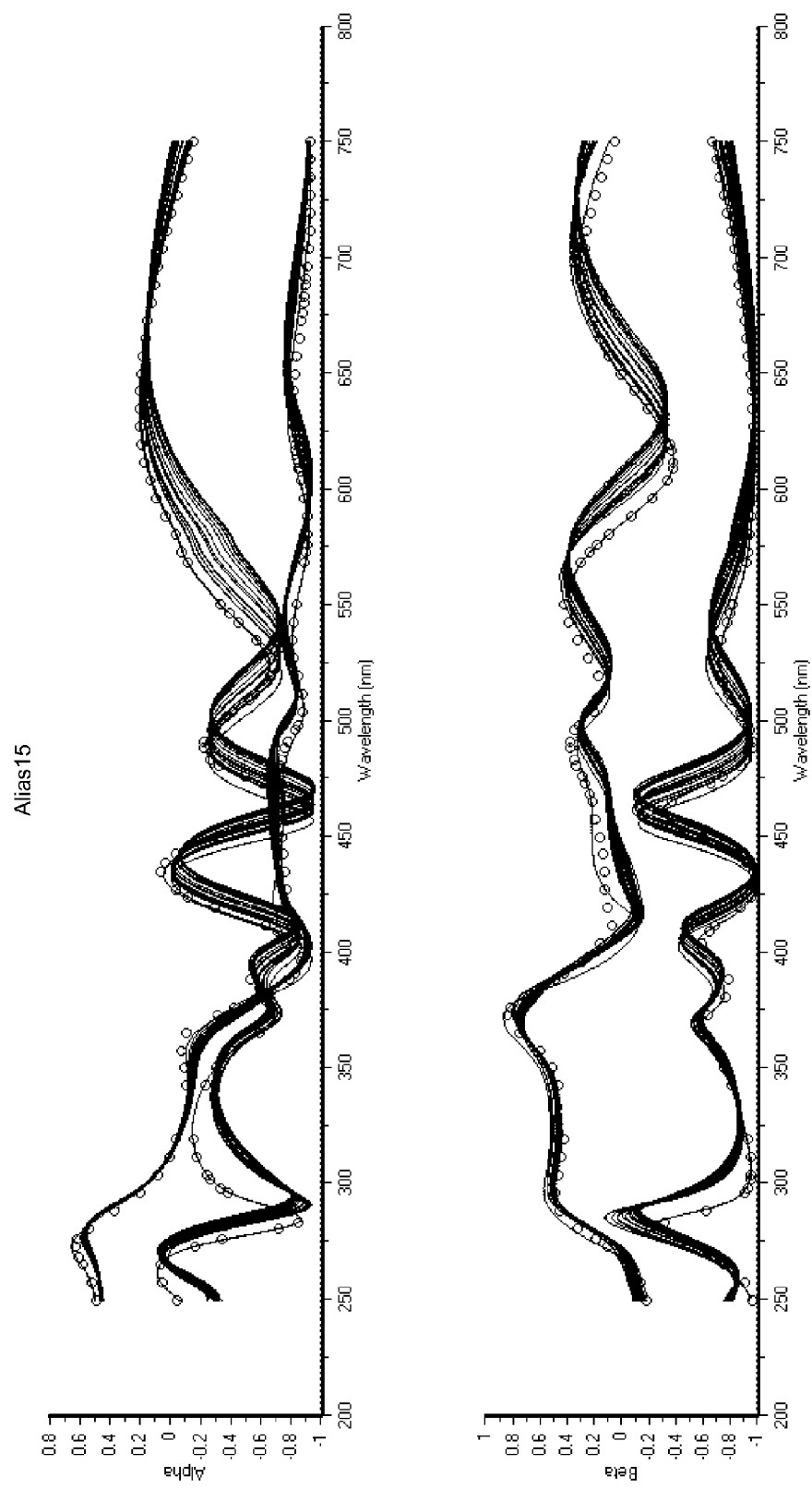
FIGS. 3A-3D show scatterometry spectra for areas of a semiconductor wafer exhibiting a grating structure with and without particle contamination.
Figure 3B:
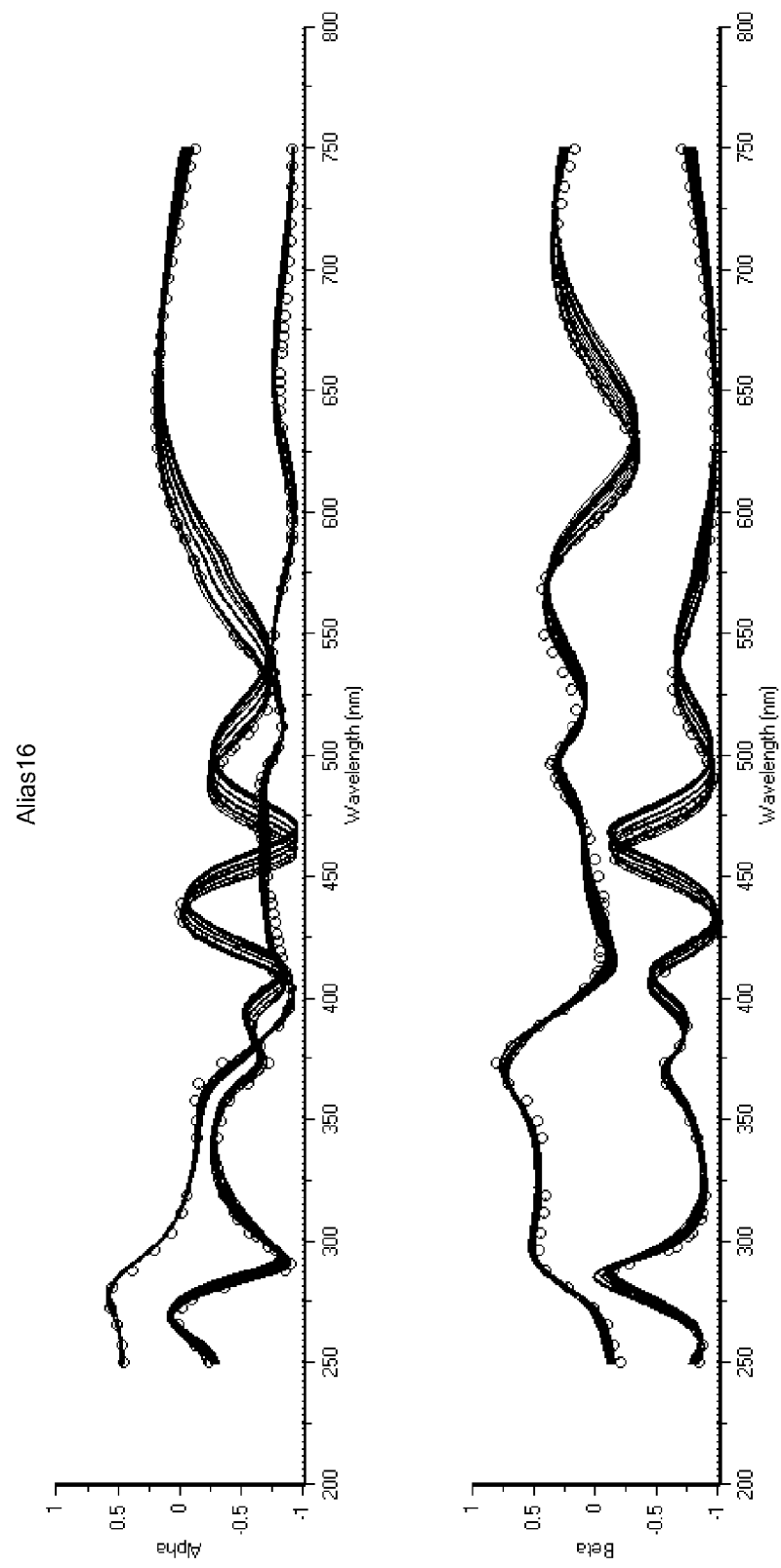
Figure 3C:
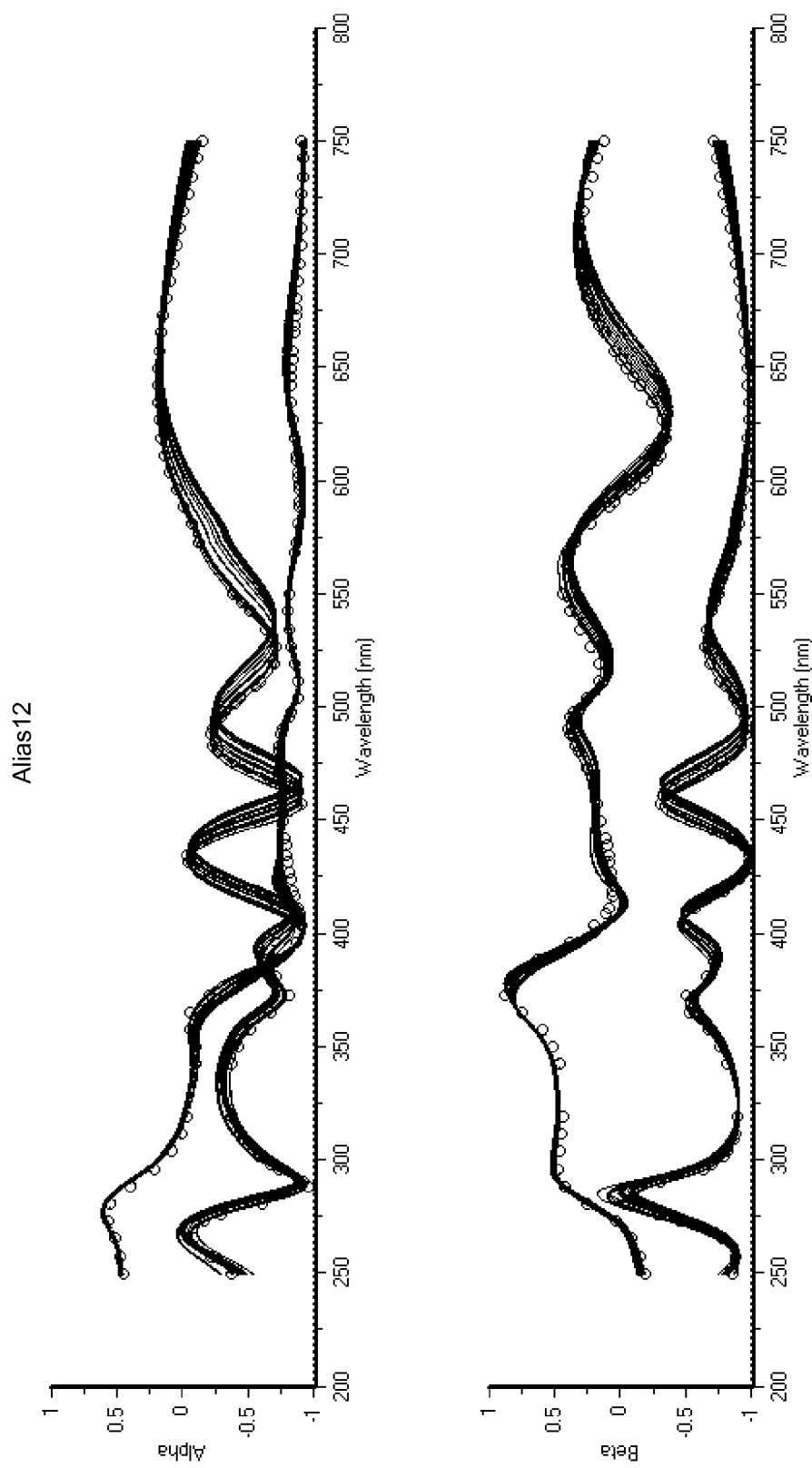
Figure 3D:
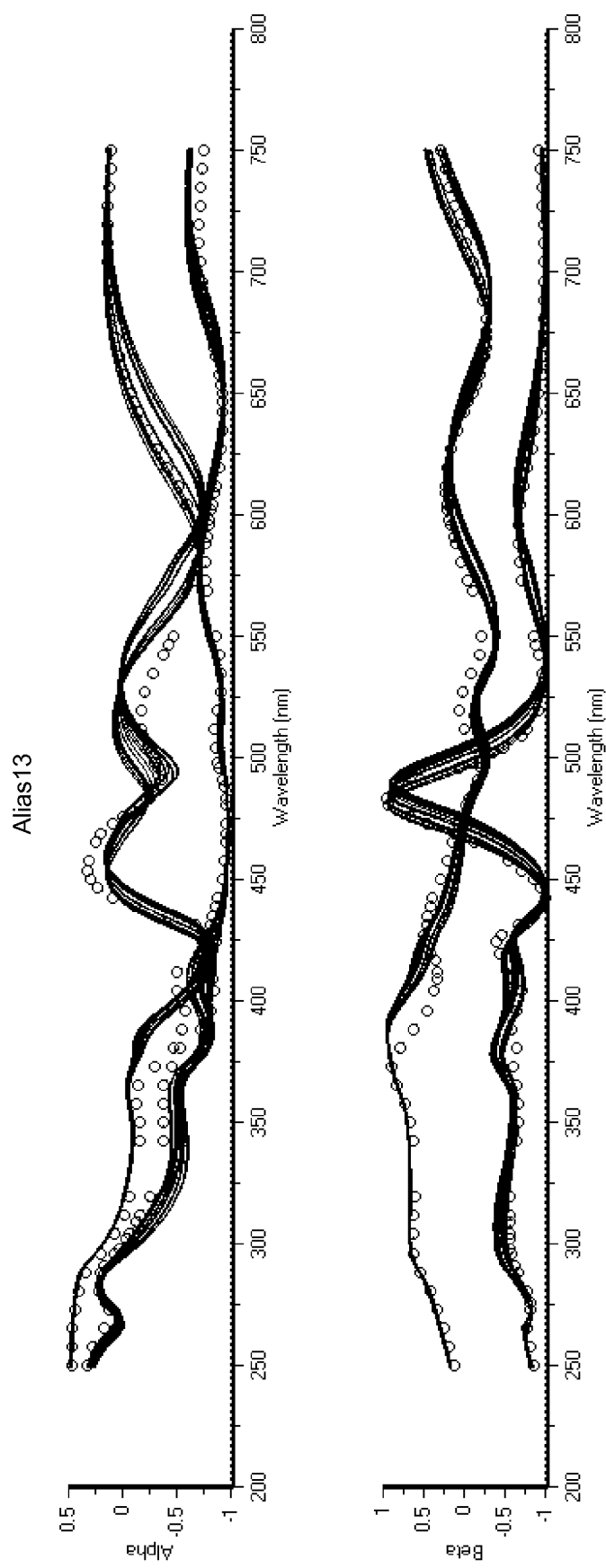

FIG. 2 shows a configuration similar to the one shown in FIG. 1. An ellipsometry tool 1100 is configured to receive a semiconductor wafer 1300 having a grating structure 1310 formed thereon according to an example of the present invention. The grating structure 1310 may be features formed in a production device on the wafer 1300 (e.g., gate electrodes, shallow trench isolation structures, interconnection trenches), or alternatively, the grating structure 1310 may be a test structure having dimensions and construction materials similar to a production device. Furthermore, the ellipsometry tool 1100 comprises a light source 1136 and a detector 1138. The detector 1138 is connected for data transfer with a data processing unit 1139. Furthermore, the ellipsometry tool 1100 comprises polarizers 1400 and 1410. The polarizer 1400 is provided for linearly polarizing the light coming from the light source 1136. Compensators as quarter wave plates or, alternatively, phase-modulators may also be employed by the ellipsometry tool 1100. By the ellipsometry tool 1100 shown in FIG. 2, a profile of change of polarization might be obtained that can be compared with stored reference profiles of change of polarization. According to one example of the present invention, the ellipsometry tool 1100 is used for the detection of particle contamination 1200. It turned out that if, in a particular area of the semiconductor wafer 1300 or the grating structure 1310, respectively, some contaminating particle 1200 is present, significant misfit of the profile of change of polarization generated for that area with the stored reference profiles of change of polarization results. This misfit that might be quantified in terms of a significantly low goodness of fitting can be used as an indicator for the presence of a contaminating particle 1200.

As already indicated, both scatterometry and ellipsometry are model based and a user may make decisions on how to construct a particular model for a particular application. In principle, the skilled person knows how to generate models and select from a stored variety of models in view of the actual application. Decisions to be made by the user include the choice of the geometric model used to describe the device. Current methodologies rely on the user to optimize the model using various metrics like parameter precision and model fit quality. Details on generating and selecting models can be found in a paper by Vaid et al. "Improved Scatterometry Time to Solutions for Leading-Edge Logic Applications," Advanced Semiconductor Manufacturing Conference, Jul. 11-13, 2010, San Francisco, Calif., IEEE/SEMI, pp. 341-346, and references therein.

Based on an actual model, reference profiles and/or spectra can be generated and stored for comparison with profiles/spectra obtained for a semiconductor wafer under investigation. In the art, best matches are to be found in order to determine characteristics of the semiconductor wafer. The present invention relates to the detection of particle contamination. Misfits of profiles, spectra or models are interpreted in terms on particle contamination. Detection of particle contamination may be facilitated by comparing profiles and/or spectra generated from light reflected from the semiconductor wafer with profiles and/or spectra representing misprocessed semiconductor wafers. For example, in addition to a database storing reference profiles/spectra, another database, a fault classification database, may be provided for storing profiles and/or spectra representing misprocessed semiconductor wafers.

If the scatterometry tool 100 of FIG. 1 or ellipsometry tool 1100 of FIG. 2 does not find a reference reflection profile that is sufficiently close to the measured reflection profile, i.e., upon failing to match the measured reflection profile to a reference reflection profile, the scatterometry tool 100 of FIG. 1 or ellipsometry tool 1100 of FIG. 2 may shift to a fault classification mode. The scatterometry tool 100 of FIG. 1 or ellipsometry tool 1100 of FIG. 2 then compares the measured reflection profile to the fault classification database to attempt to characterize the processing fault. The fault classification database includes a library of misprocessed reflection profiles associated with known processing faults. For example, the fault classification library may include misprocessed reflection profiles for features that were formed with missing, extra or incorrect process layers. Thus, it can be excluded that a misfit is rather caused by some misprocessing than by the presence of a contaminating particle. However, particle contamination may result in a very characteristic abnormal profile and/or spectrum.

FIGS. 3A-3D show typical scatterometry spectra (scatterometric parameters alpha and beta versus wavelength) for four different areas of a grating structure of a semiconductor wafer similar to the grating structure 310 shown in FIG. 1 and the grating structure 1310 shown in FIG. 2. The spectra (Alias 12, 15 and 16) obtained for areas without particle contamination significantly differ from the spectra (Alias 13) obtained for an area including a contaminating particle, in the present case, an SiGe or Si particle. The physical reason for the differences can be seen in the reflectivity of the contamination particles. The random shapes of the contaminating particles cannot be modeled by current scatterometry modeling that is based on spatially periodic structures (for example, Maxwell solvers).

Figure 5A:
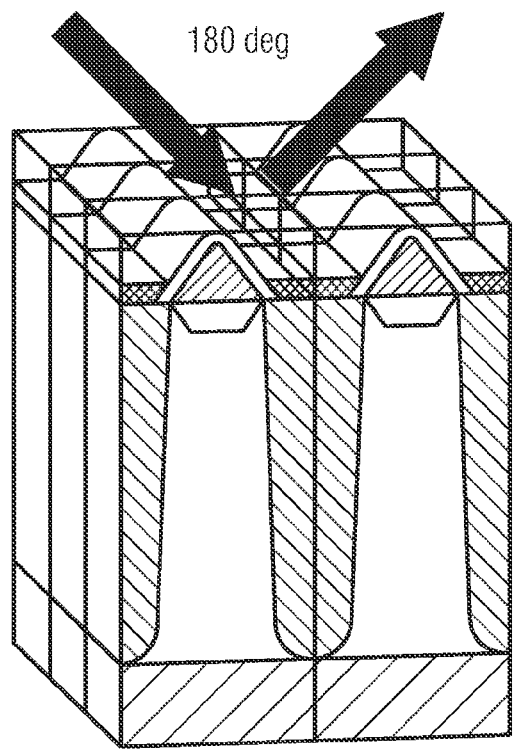
FIGS. 5A-5B illustrate 90° and 180° orientation of the scatterometric examination of a grating structure of a semiconductor wafer under investigation.
Figure 5B:
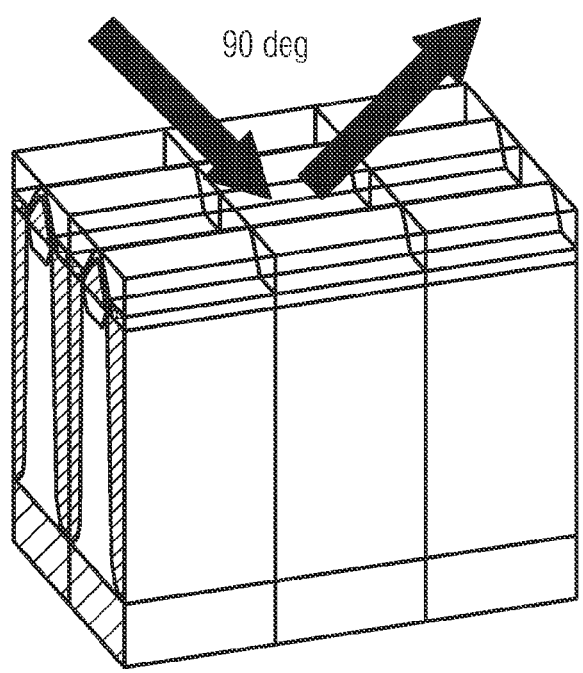

Note that, in the example shown in FIGS. 3A-3D, for each sample spectra, two scatterometric orientations, 90° and 180°, are shown. The scatterometric orientations 90° and 180° are illustrated in FIGS. 5A and 5B. By 90° orientation, incidence and reflection of light substantially parallel to gratings, for example, gate electrode structures, is meant. By 180° orientation, incidence and reflection of light substantially perpendicular to gratings, for example, gate electrode structures, is meant. As can be seen from FIGS. 3A-3D, the spectra and correlations of the spectra for both orientations for particle contamination (Alias 13) significantly differ from the cases of no particle contamination (Alias 12, 15 and 16). The abnormal spectra obtained for the areas of the semiconductor wafer exhibiting particle contamination result in misfits with modeled features, for example, the overlay structure and thicknesses of layers and spacer elements. The misfits can be characteristic for particle contamination and can thus be indicative for particle contamination.

Figure 4A:
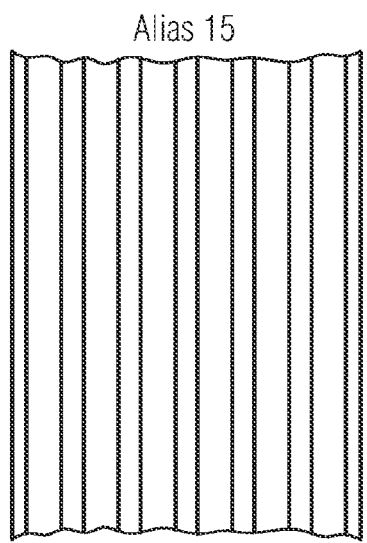
FIGS. 4A-4E show particles identified by inline scanning electron microscopy proving the concept of the present invention.
Figure 4B:
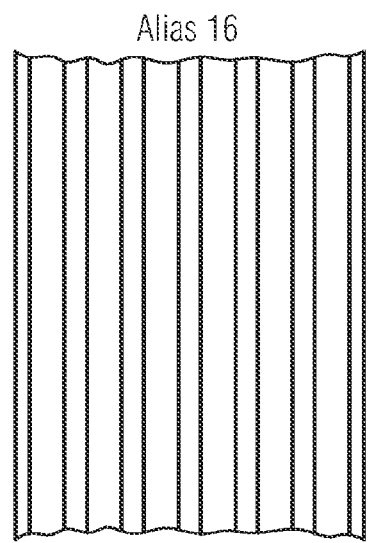
Figure 4C:
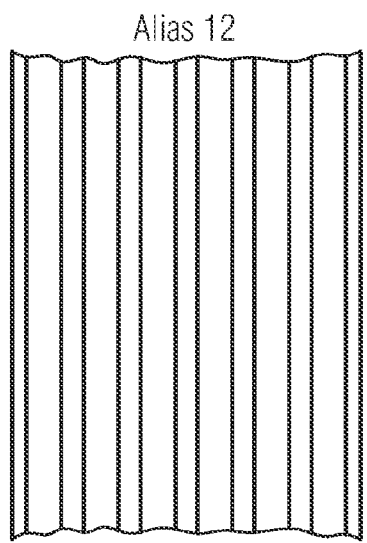
Figure 4D:
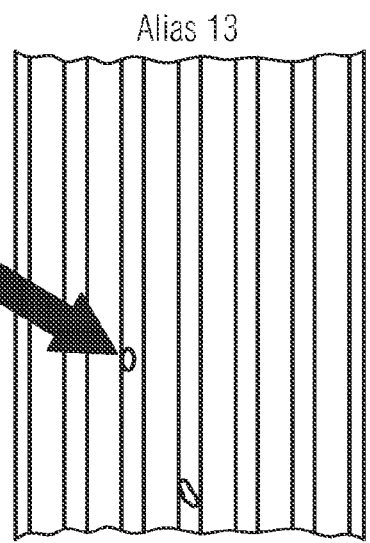
Figure 4E:
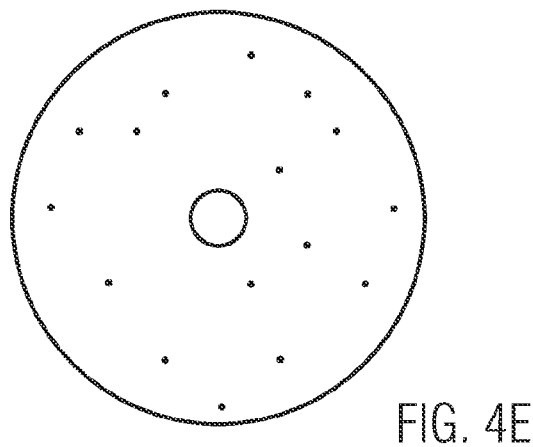

It is stressed that the new unusual usage of scatterometry and ellipsometry for contamination detection may be combined with inline scanning electron microscopy. For example, a low goodness of fitting determined for a scatterometric or ellipsometric spectrum for a certain dye is taken as evidence for a high probability of presence of a contaminating particle (see FIGS. 3A-3D). A measurement spot of the obtained spectrum may have dimensions of 50 times 50 micrometers or 20 times 20 micrometers, for instance. The scatterometry or ellipsometry tool sends a feedback for the low goodness of fitting including coordinates of the location measured with the low goodness of fitting to an inline scanning electron microscope that is used for defect identification for this particular location. The defect can then be identified and classified based on the measurements of the inline scanning electron microscope illustrated in FIGS. 4A-4E; FIG. 4D corresponds to Alias 13 shown in FIG. 3D).

As a result, the present disclosure provides fast and non-destructive methods for the detection of particle contamination. The methods employ scatterometry or ellipsometry in an atypical manner. Whereas conventionally scatterometry and ellipsometry are used for determining characteristics as the thicknesses of layers formed on a semiconductor wafer and the overlay structure of the same, according to the present invention, scatterometry or ellipsometry provides abnormal reflection profiles and spectra that do not match with reference profiles and spectra. The misfit with modeled reference profiles and spectra is indicative of the presence of a contaminating particle on the semiconductor wafer under investigation. Scatterometric models of a semiconductor wafer with contaminating particles show incorrect values and a low goodness of fitting. This information can effectively and reliably be used for the detection of particle contamination.

The particular embodiments disclosed above are illustrative only, as the invention may be modified and practiced in different but equivalent manners apparent to those skilled in the art having the benefit of the teachings herein. For example, the process steps set forth above may be performed in a different order. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed:

1. A method for detecting contaminating particles on a semiconductor wafer comprising a grating structure, comprising:
   examining an area of the semiconductor wafer including said grating structure by a metrology system comprising a scatterometry, ellipsometry or reflectometry tool to obtain measured metrology data regarding contaminating particles in the area by illuminating at least a portion of said grating structure and measuring light reflected from said grating structure to generate a reflection profile;
   comparing said measured metrology data with reference metrology data comprising reference reflection profiles of reference grating structures with contaminating particles disposed on surfaces thereof; and
   determining the presence of at least one contaminating particle disposed on a surface of the grating structure and separate from said grating structure in the examined area of said semiconductor wafer based on the comparison of said measured metrology data with said reference metrology data.

2. The method of claim 1, wherein the step of determining the presence of the at least one contaminating particle in the examined area of said semiconductor wafer comprises determining if said generated reflection profile correlates with any of said reference reflection profiles.

3. The method of claim 1, wherein said semiconductor wafer is a wafer having a grating structure and wherein examining said area of said semiconductor wafer comprises illuminating at least a portion of said grating structure by polarized light and detecting light reflected from said grating structure to determine a profile of polarization or change of polarization, and wherein said reference metrology data comprises reference profiles of polarization or change of polarization for said grating structure with contaminating particles.

4. The method of claim 1, wherein said semiconductor wafer is a wafer having a grating structure and wherein examining said area of said semiconductor wafer comprises illuminating at least a portion of said grating structure and measuring light reflected from said grating structure to generate a measured scatterometric spectrum, and
   wherein said reference metrology data comprises reference scatterometric spectra for said grating structure with contaminating particles.

5. The method of claim 4, wherein the presence of the at least one contaminating particle in the examined area of said semiconductor wafer is determined based on a difference between the measured scatterometric spectrum and at least one of said reference scatterometric spectra for said grating structure with contaminating particles.

6. The method of claim 4, wherein said reference scatterometric spectra are obtained based on a scatterometric model and further comprising determining a goodness of fitting of said scatterometric model and said measured scatterometric spectrum and wherein the presence of contaminating particles in the examined area of said semiconductor wafer is determined based on the determined goodness of fitting.

7. The method of claim 1, further comprising examining said area of said semiconductor wafer with a first orientation of incidence and reflection of light used for illuminating said area and a second orientation of incidence and reflection of light used for illuminating said area, wherein said second orientation is perpendicular to said first orientation.

8. The method of claim 1, further comprising sending a feedback on possible contaminating particle detection to a scanning electron microscope and verifying the presence of the at least one contaminating particle in the examined area by said scanning electron microscope.

9. A metrology tool adapted to receive a semiconductor wafer, comprising
a light source adapted to illuminate at least a portion of said semiconductor wafer comprising a grating structure;
a detector adapted to measure light reflected from said semiconductor wafer;
a database storing reference metrology data regarding contaminating particles disposed on surfaces of grating structures; and
a data processing unit adapted to obtain measured metrology data regarding contaminating particles disposed on said grating structure based on said reflected light measured by said detector, compare said measured metrology data with said reference metrology data and determine the presence of at least one contaminating particle disposed on a surface of the grating structure and separate from said grating structure in the examined area of said semiconductor wafer based on the comparison of said measured metrology data with said reference metrology data.

10. The metrology tool of claim 9, further comprising a scatterometry, ellipsometry or reflectometry tool comprising said light source and said detector.

11. The metrology tool of claim 9, wherein said database stores reference reflection profiles of contaminating particles and wherein said data processing unit is adapted to generate a reflection profile from said reflected light measured by said detector and determine the presence of the at least one contaminating particle in the examined area of said semiconductor wafer by determining if the generated reflection profile correlates with any of the stored reference reflection profiles.

12. The metrology tool of claim 9, wherein said reference metrology data comprises reference profiles of change of polarization of contaminating particles and further comprising an ellipsometry tool comprising the light source polarizer for illuminating said at least a portion of said semiconductor wafer by polarized light and wherein said data processing unit is adapted to determine a profile of polarization or change of polarization of the reflected light measured by said detector and determine the presence of the at least one contaminating particle in the examined area of said semiconductor wafer based on a comparison of the determined profile of polarization or change of polarization with said reference profiles of polarization or change of polarization.

13. The metrology tool of claim 9, wherein said reference metrology data comprises reference scatterometric spectra of contaminating particles and wherein said data processing unit is adapted to generate a measured scatterometric spectrum and determine the presence of the at least one contaminating particle in the examined area of said semiconductor wafer based on the comparison of said measured scatterometric spectrum with said reference scatterometric spectra.

14. The metrology tool of claim 13, wherein said data processing unit is adapted to determine the presence of the at least one contaminating particle based on a difference between said measured scatterometric spectrum and at least one of said reference scatterometric spectra.

15. The metrology tool of claim 12, wherein said reference scatterometric spectra represent results of a scatterometric model and wherein said data processing unit is adapted to determine a goodness of fitting of said scatterometric model and said measured scatterometric spectrum and determine the presence of the at least one contaminating particle based on the determined goodness of fitting.

* * * * *